United States Patent
Hasumi et al.

(10) Patent No.: US 7,476,515 B2
(45) Date of Patent: Jan. 13, 2009

(54) AFFINITY TRAP REACTOR AND SINGLE-STEP PROCESS FOR PURIFYING ANGIOSTATIN-LIKE FRAGMENT FROM HUMAN PLASMA USING THE SAME

(75) Inventors: Keiji Hasumi, Inagi (JP); Kosuke Shimizu, Fuchu (JP)

(73) Assignee: TTC Co., Ltd., Tokyo (JP)

( * ) Notice: Subject to any disclaimer, the term of this patent is extended or adjusted under 35 U.S.C. 154(b) by 193 days.

(21) Appl. No.: 10/541,228

(22) PCT Filed: Jan. 17, 2003

(86) PCT No.: PCT/JP03/00338

§ 371 (c)(1),
(2), (4) Date: Jun. 29, 2005

(87) PCT Pub. No.: WO2004/065595

PCT Pub. Date: Aug. 5, 2004

(65) Prior Publication Data

US 2006/0134721 A1    Jun. 22, 2006

(51) Int. Cl.
  *C12Q 1/37*    (2006.01)
  *C12P 21/06*    (2006.01)
  *C12P 1/00*    (2006.01)

(52) U.S. Cl. .................. 435/23; 435/41; 435/68.1

(58) Field of Classification Search .................. 435/183
  See application file for complete search history.

(56) References Cited

U.S. PATENT DOCUMENTS 4,224,125 A    9/1980    Nakamura et al.
5,227,297 A *  7/1993    Patel et al. .................. 435/174
6,228,613 B1 * 5/2001    Fischer et al. .............. 435/69.1
6,528,299 B1 * 3/2003    Romisch et al. ............. 435/219

FOREIGN PATENT DOCUMENTS

EP    0 881 287 A2    12/1998

(Continued)

OTHER PUBLICATIONS

Stegmayr, B.G., Transfusion and Apheresis Science, 2005, 32, 209-220.*

(Continued)

*Primary Examiner*—Sandra E Saucier
*Assistant Examiner*—Aaron J Kosar
(74) *Attorney, Agent, or Firm*—Frishauf, Holtz, Goodman & Chick, P.C.

(57) ABSTRACT

The present invention provides an affinity trap reactor that enables the reaction between an enzyme bound to a support and substrate to proceed efficiently without its applications being restricted by the type of enzyme and substrate used. The present invention relates to an affinity trap reactor composed of a support bound with an enzyme and a molecule that specifically binds with a substrate of the enzyme, and a single-stage process for obtaining BL-angiostatin from plasminogen contained in a biological sample, wherein a biological sample containing plasminogen is applied to an affinity trap reactor composed of a support bound with bacillolysin MA and lysine, and reacted under conditions of a temperature of 0 to 50° C. in the presence of isopropyl alcohol but in the absence of calcium ions.

11 Claims, 1 Drawing Sheet

FOREIGN PATENT DOCUMENTS

| EP | 1 111 385 A2 | | 6/2001 |
|---|---|---|---|
| JP | 55141193 A | * | 11/1980 |
| JP | 2002-272453 A | | 9/2002 |

OTHER PUBLICATIONS

Soff, G.A., Cancer and Metastasis Reviews.2000,19,97-107.*
Arne Östman and Frank-D. Böhmer. Trends in Cell Biology, 2001,11(6), 258-266.*
Bizik, J; Vaheri, A. Pathophysiology. 1998, 5(Supplement 1), 139.*
McClung, W.G., et al.Journal of Biomedical Materials Research. 2000,49(3),409-414.*
Narasaki, R, et al. "Bacillolysin MA, a novel bacterial metalloproteinase that produces angiostatin-like fragments from plasminogen and activates protease zymogens in the coagulation and fibrinolysis systems" J. Biol. Chem. 2005,280(14),14278-87.*
Kosuke Shimizu, Ritsuko Narasaki, Harushige Kuribayashi, Tsutomu Sato, and Keiji Hasumi. "One step purification of angiostatin from plasma using a new processing protease bacillolysin MA" Journal of Biochemistry. Aug. 2002, 74(8), 4P-459 (English Translation) and supplemental figures.*
Keiji Hasumi, "A New Microbiological Enzyme which Catalyzes Angiostatin Conversion of Plasminogen," Mishima Kaiun Memorial Foundation, Research Report, No. 39, (2001), 60-64 (English abstract, English portions of text, and figures only).*
Keiji Hasumi, "A New Microbiological Enzyme which Catalyzes Angiostatin Conversion of Plasminogen," Mishima Kaiun Memorial Foundation, Research Report FY2001, No. 39, Dec. 1, 2002, 60-64. (English Translation).*
M.S. O'Reilly, et al., "Angiostatin: A Novel Angiogenesis Inhibitor That Mediates the Suppression of Metastases by a Lewis Lung Carcinoma," *Cell*, (USA), Oct. 21, 1994, vol. 79, No. 2, pp. 315 to 328.
M.S. O'Reilly et al., "Angiostatin Induces and Sustains Dormancy of Human Primary Tumors in Mice," *Nature Medicine*, (USA), 1996, vol. 2, No. 6, pp. 689 to 692.
B.K. Sim et al., "A Recombinant Human Angiostatin Protein Inhibits Experimental Primary and Metastic Cancer," *Cancer Research*, (USA), 1997, vol. 57, pp. 1329 to 1334.

* cited by examiner

AFFINITY TRAP REACTOR AND SINGLE-STEP PROCESS FOR PURIFYING ANGIOSTATIN-LIKE FRAGMENT FROM HUMAN PLASMA USING THE SAME

CROSS-REFERENCE TO RELATED APPLICATION

This application is a United States national phase application under 35 USC 371 of International application PCT/JP2003/000338 filed on Jan. 17, 2003.

TECHNICAL FIELD

The present invention relates to an affinity trap reactor in which an enzyme such as a protease is immobilized.

BACKGROUND ART

Substances that inhibit vascular neogenesis are expected to be applied as antitumor agents since they inhibit cancer growth, invasion and metastasis, and angiostatin is known to be one of such substances. Angiostatin is a protein having a molecular weight of about 40,000 that is obtained by the degradation of a fibrinolytic factor, plasminogen, present in blood. It has been reported to demonstrate dramatic effects against cancer in animal studies (see Non-Patent Document 1). There are two methods used to produce angiostatin, namely (1) hydrolyzing plasminogen with a protease known as elastase (see Non-Patent Document 2), and (2) producing it directly in *Escherichia coli* using gene recombination technology (see Non-Patent Document 3). In the case of method (1), there is considerable formation of by-products due to the low substrate-specificity of elastase, thus making it difficult to selectively form angiostatin from plasminogen. In addition, this method also has the disadvantage of the activity of the resulting angiostatin being low. In the case of method (2), it is difficult to purify angiostatin produced from *E. Coli,* and considerable costs are incurred. In addition, there is also a problem with the low level of solubility. Consequently, there has been a need to develop a means of obtaining angiostatin at high purity using a simple method.

Recently, a protease produced by *Bacillus megaterium* strain A9542 known as bacillolysin MA has been observed to form an angiostatin-like fragment having angiogenesis inhibitory action by specifically severing plasminogen (comprising mainly of $Glu^1$-$Ser^{441}$, hereinafter referred to as BL-angiostatin), and a mini-plasminogen-like fragment having thrombolytic activity (comprising mainly of $Val^{442}$-$Asn^{791}$) (see Patent Document 1). Since this enzyme known as bacillolysin MA is extremely stable, it can be used in various applications by immobilizing on a support. Therefore, there is a need to develop a process for obtaining highly pure BL-angiostatin by carrying out the steps from the reaction of bacillolysin MA and substrate plasminogen to purification of the resulting product BL-angiostatin in a single stage using the characteristics of bacillolysin MA, and to develop a device for carrying out that process.

On the other hand, enzyme-immobilized reactors in which various enzymes such as protease which can be used for various uses are immobilized on a support for use in a reaction have been proposed in the prior art. However, proteases are susceptible to inactivation resulting from degradation of the immobilized protease due to self-digestion, and in the case the substrate of the enzyme such as protease has a high molecular weight, the reaction between the enzyme bound to the support and the substrate has difficulty in proceeding efficiently and rapidly due to spatial restrictions. For these reasons, the applications of enzyme-immobilized reactors are limited by the types of enzymes and substrates used, and expectations have been placed on the development of an enzyme-immobilized reactor that can be widely used for various types of enzymes and substrates.

Patent Document 1: Japanese Unexamined Patent Publication No. 2002-272453

Non-Patent Document 1: M. S. O'Reilly, et al., Cell (USA), Oct. 21, 1994, Vol. 79, No. 2, pp. 315-328

Non-Patent Document 2: M. S. O'Reilly, et al., Nature Medicine (USA), 1996, Vol. 2, pp. 689-692

Non-Patent Document 3: B. K. Sim, et al., Cancer Research (USA), 1997, Vol. 57, pp. 1329-1334

As a result of conducting extensive research to develop an enzyme-immobilized reactor free of the aforementioned problems, as well as a process of producing BL-angiostatin using the characteristics of the aforementioned bacillolysin MA, the inventor of the present invention found that, by binding an enzyme such as bacillolysin MA together with a molecule that specifically binds with an enzyme substrate to a support to compose an affinity trap reactor, together with obtaining a reactor that is free of the aforementioned problems, by using an affinity trap reactor in which bacillolysin MA is immobilized as the enzyme and Lys is immobilized as the molecule that specifically binds with the enzyme substrate, a process is obtained for highly efficiently and rapidly degrading and purifying BL-angiostatin from plasminogen contained in biological samples such as blood, thereby leading to completion of the present invention.

DISCLOSURE OF THE INVENTION

The present invention relates to an affinity trap reactor comprising a support on which are bound an enzyme and a molecule that specifically binds with the enzyme substrate. Moreover, the present invention relates to a process for obtaining BL-angiostatin from plasminogen contained in a biological sample in a single stage, wherein a biological sample containing plasminogen is applied to an affinity trap reactor composed of a support on which are bound bacillolysin MA and lysine, and allowed to react under conditions of a temperature of about 0° C. to 50° C., and preferably about 4° C. to 25° C., in the presence of isopropyl alcohol but in the absence of calcium ions, to obtain BL-angiostatin at high purity.

BEST MODE FOR CARRYING OUT THE INVENTION

Figure 1:
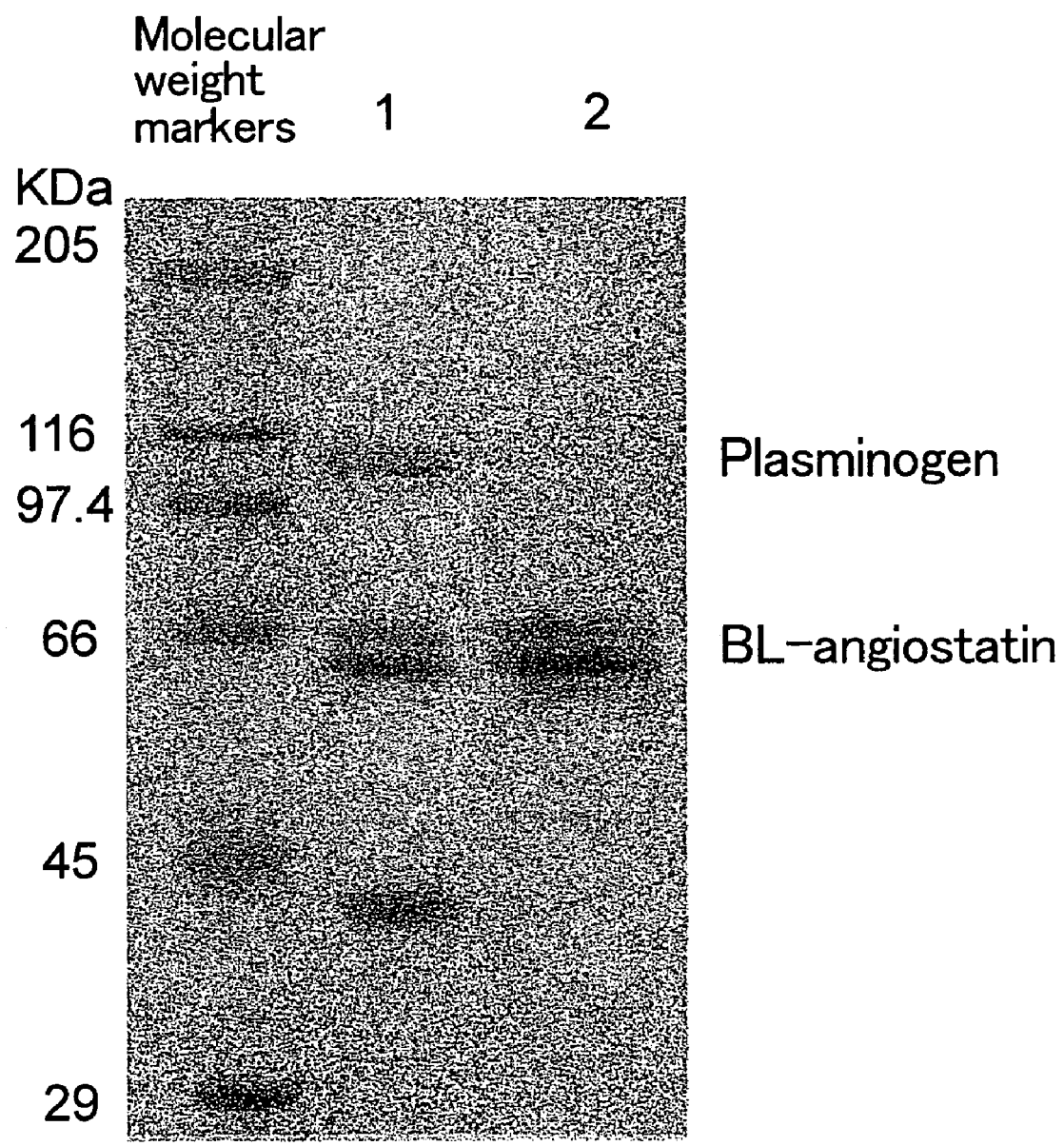
FIG. 1 is an electropherogram of BL-angiostatin obtained by degrading plasminogen with bacillolysin.

Affinity Trap Reactor of the Present Invention

The affinity trap reactor of the present invention is composed of a support on which are bound and immobilized an enzyme and a molecule that specifically binds with the enzyme substrate. As a result of binding both an enzyme and a molecule that specifically binds the enzyme substrate on a support, and the enzyme substrate being trapped and bound to the support through the molecule, steric hindrance is minimized and an environment is formed in which the substrate and enzyme are locally concentrated, thereby enabling the reaction between the enzyme and substrate to proceed stably, highly efficiently and rapidly.

Various types of enzymes can be used as necessary as the enzyme immobilized on the affinity trap reactor of the present invention provided it is an enzyme that can be immobilized on the support by covalent bonding. Various types of enzymes can be used, examples of which include hydrolases including proteases, glycosidases and lipases, oxidoreductases, transferases, lyases, isomerases and synthetases.

Molecules bound to the support that specifically bind with the enzyme substrate are molecules that specifically and reversibly bind with the enzyme substrate through a low molecular weight ligand or antigen-antibody reaction and so forth, and any molecule can be used as necessary provided it is a molecule that can be bound to the support. For example, by selecting and binding a molecule that specifically binds with the enzyme substrate and the desired reaction product but does not bind to reaction by-products, the reaction by-products can be easily removed from the affinity trap reactor following the enzyme reaction, thereby making it possible to recover only the desired product at high yield. Examples of enzymes, substrates and molecules that specifically bind therewith are shown below.

TABLE 1

| Enzyme | Substrate | Molecule Specifically Binding with Substrate |
| --- | --- | --- |
| Bacillolysin MA | Plasminogen | Lysine |
| Bacillolysin MA | Prothrombin | Hirudine, anti-thrombin antibody |
| Trypsin | Preproinsulin | Anti-insulin antibody, Fab fragment |

As indicated above, in the case the enzyme bound to the support is bacillolysin MA, an enzyme produced by *Bacillus megaterium* strain A9542, lysine (Lys) can be preferably used for the molecule that specifically binds with the enzyme substrate. In this case, although lysine specifically binds with the substrate, plasminogen and the desired degradation product, BL-angiostatin, it does not bind with the by-product, mini-plasminogen. Consequently, after the enzyme reaction, since the by-product is removed from the affinity trap reactor without being bound to the support, only the desired product can be selectively recovered.

A support capable of being used in the affinity trap reactor of the present invention can be suitably selected and used by a person with ordinary skill in the art depending on the immobilized enzyme and type and properties of the molecule that specifically binds with the substrate, provided it is a support that is normally used in affinity chromatography. Examples of supports that can be used include porous silica bead supports; cellulose-based supports such as Cellex, Cellex AE, Cellex CM and Cellex PAB (all manufactured by Selva); agarose-based supports such as Sepharose 2B, Sepharose 4B and Sepharose 6B (all manufactured by Pharmacia); crosslinked dextran-based supports such as Sephadex and CM-Sephadex (both manufactured by Pharmacia); and crosslinked polyacrylamide-based supports such as Chromagel P, Enzafix P-HZ, Enzafix P-SH and Enzafix P-AB (all manufactured by Wako Pure Chemical Industries). In particular, bead-like supports in the form of agarose-based supports such as Sepharose 2B, Sepharose 4B and Sepharose 6B can be used preferably for reasons such as superior stability and mechanical properties, high ligand fixation capacity and low non-specific adsorption. In the case of using agarose gel, it is preferable to activate the gel in advance using a cyanogen halide (cyanogen bromide, cyanogen iodide or cyanogen chloride).

Although the aforementioned enzyme may be bound directly to a support, it may also be bound through a spacer group as necessary. For example, a spacer group can be used in the case the support and enzyme cannot be coupled by direct chemical bonding, or in the case the enzyme is a comparatively small molecule and it is difficult to carry out binding between the enzyme and substrate completely. Such a spacer group can be suitably selected by a person with ordinary skill in the art according to the type of enzyme bound. On the other hand, in the case of binding bacillolysin MA to a support, it can be bound directly to the support without using a spacer in particular.

Examples of supports and enzymes able to be used preferably in the affinity trap reactor of the present invention, its substrates, molecules able to specifically bind with substrate, and spacer groups that can be used are indicated below, but the affinity trap reactor of the present invention is not limited thereto.

TABLE 2

| Support | Enzyme | Substrate | Molecule Specifically Binding with Substrate | Spacer |
| --- | --- | --- | --- | --- |
| Agarose gel | Bacillolysin MA | Plasminogen | Lysine | None |
| Agarose gel | Bacillolysin MA | Prothrombin | Hirudine, anti-thrombin antibody | None |
| Agarose gel | Trypsin | Preproinsulin | Anti-insulin antibody, Fab fragment | None |

Production of Affinity Trap Reactor of the Present Invention

Since an affinity trap reactor of the present invention has an enzyme and a molecule that specifically binds with the substrate of the enzyme bound to a support, it can be easily produced by a person with ordinary skill in the art by applying a method of producing affinity chromatography used in the field of biochemistry.

During this production, an enzyme is first bound to the support being used. During binding, binding between the support and enzyme is facilitated by activating a functional group of the support as necessary. For example, in the case of using agarose gel for the support, the agarose gel is activated by pretreating with a halogenated cyanogen (such as cyanogen bromide, cyanogen iodide or cyanogen chloride). Activated agarose gels are also available commercially, and these can also be used.

The activated support is washed with a buffer as necessary, and the support is treated with an enzyme solution dissolved in the same buffer to bind the enzyme to the support. The concentration of enzyme contained in the buffer can be suitably determined depending on the type of immobilized enzyme. In addition, the buffer composition, pH and reaction time and so forth used here can also be suitably determined depending on the type of immobilized enzyme. For example, in the case of immobilizing bacillolysin MA on a support, a buffer having a pH of 8 to 9 (composition: 0.1 M sodium hydrogen carbonate, pH 8.3, and additionally containing roughly 0.5 M NaCl and roughly 5% isopropyl alcohol) containing about 0.5 to 10 mg/ml, and preferably about 2.84 mg/ml, of bacillolysin MA, is used and allowed to react for about 2 hours.

Next, the enzyme solution is removed by a means such as aspiration, and then the support is treated with an aqueous solution containing a molecule that specifically binds with the enzyme substrate to bind the molecule that specifically binds with the enzyme substrate to the support. The concentration of molecule that specifically binds with the enzyme substrate and the reaction time can be suitably determined depending on the type of molecule. In the case of using lysine as the molecule, a roughly 5% aqueous isopropyl alcohol solution containing about 0.1 to 1 M, and preferably about 0.2 M, lysine hydrochloride, is used and allowed to react for about 2 hours. The reaction can be carried out at room temperature.

Next, an affinity trap reactor of the present invention is obtained by removing the aqueous solution of a molecule that specifically binds with the enzyme substrate by a means such as aspiration, and washing the support on which are bound the enzyme and molecule that specifically binds with the enzyme substrate with a buffer. Although the type of buffer can be suitably selected depending on the type of immobilized enzyme and molecule that specifically binds with the enzyme substrate, in the case of a reactor in which bacillolysin MA and lysine are bound, the support can be washed with a buffer such as 20 mM MES (2-(morpholino)ethanesulfonic acid)-NaOH buffer (pH 6.5) (Buffer B).

The concentration of isopropyl alcohol contained in the buffer or aqueous solution used in each of the steps for producing the aforementioned reactor in which bacillolysin MA and lysine are bound is about 1 to 10%, and preferably about 5%. As a result of carrying out each of the steps in the presence of isopropyl alcohol, inactivation of the enzyme immobilized on the support can be prevented, and the enzyme can be kept stable for a long period of time.

Furthermore, the order in which the aforementioned enzyme and molecule that specifically binds with the enzyme substrate are bound to the support is such that either can be bound first.

An affinity trap reactor of the present invention obtained in this manner is stored in a buffer containing about 0.01 to 0.1%, and preferably about 0.02%, sodium azide at a low temperature of about 0 to 5° C., and preferably about 4° C. The type of buffer can be suitably selected. In the case of a reactor bound with bacillolysin MA and lysine, it can be stored in a buffer such as 20 mM MES (2-(morpholino)ethanesulfonic acid)-NaOH buffer (pH 6.5) containing about 0.02% sodium azide. As a result of storing at a low temperature in a sodium azide solution in this manner, an affinity trap reactor of the present invention can be stored stably for a long period of time without causing deactivation of the enzyme.

With the constitution described above, affinity trap reactor of the present invention allows the reaction between enzyme and substrate to proceed at high efficiency and specifically without placing limitations on the type of enzyme immobilized or type of molecule that specifically binds with the enzyme substrate.

Use of an Affinity Trap Reactor of the Present Invention

In order for the desired reaction between an enzyme and substrate to proceed using an affinity trap reactor of the present invention, an affinity trap reactor of the present invention prepared as previously described is equilibrated in advance with a buffer. The type of buffer can be suitably selected depending on the type of immobilized enzyme and molecule that specifically binds the enzyme substrate. For example, in the case of an affinity trap reactor of the present invention bound with bacillolysin MA for the enzyme and lysine for the molecule that specifically binds enzyme substrate, a 50 mM sodium phosphate buffer containing about 1 to 10%, and preferably about 5%, of isopropyl alcohol (pH 7.4) (Buffer C), can be used.

Next, supernatant is obtained by centrifuging a sample such as biological sample (e.g. as blood) that contains the substrate of the enzyme immobilized on the affinity trap reactor. In the case of an affinity trap reactor of the present invention bound with bacillolysin MA for the enzyme and lysine for the molecule that specifically binds its substrate, isopropyl alcohol is preliminarily added to the biological sample such as plasma over ice prior to centrifugation. The concentration of the isopropyl alcohol following addition is about 1 to 10%, and preferably about 5%. The conditions of centrifugation can be suitably determined depending on the type of sample. The reaction between the substrate in the biological sample and the enzyme is allowed to proceed by adding the resulting supernatant to the equilibrated affinity trap reactor of the present invention, after which the affinity trap reactor is washed with a buffer, and the product formed by the enzyme reaction is eluted by adding an eluate. The buffer used for equilibration can be used for the buffer used to wash the reactor. For example, in the case of an affinity trap reactor of the present invention bound with bacillolysin MA for the enzyme and lysine for the molecule that specifically binds with its substrate, the reactor is washed with the aforementioned Buffer C containing about 0.5 M NaCl. The eluate can also be suitably determined depending to the type of enzyme and substrate. For example, in the case of an affinity trap reactor bound with bacillolysin MA for the enzyme and lysine for the molecule that specifically binds with its substrate, about 1 to 10%, and preferably about 5%, aqueous isopropyl alcohol containing about 200 mM 6-aminohexanoic acid can be used as the eluate.

In the case of an affinity trap reactor bound with bacillolysin MA for the enzyme and lysine for the molecule that specifically binds with its substrate, all of the aforementioned series of reactions are carried out at a temperature of about 0 to 50° C., and preferably about 4 to 25° C. By allowing the reactions to proceed at this temperature, not only is the bacillolysin MA immobilized on the affinity trap reactor kept stable without self-digesting, but the minimum required action of bacillolysin MA on plasminogen is ensured, thereby enabling the enzyme reaction to proceed smoothly and specifically. In addition, each reaction is allowed to proceed under the conditions that calcium ions are not contained in each buffer used in the series of reactions and there are no calcium ions present in the reactions.

Following use, an affinity trap reactor of the present invention is stored in a buffer containing sodium azide after washing with buffer. Although the type of buffer can be suitably selected, the buffer used to equilibrate the affinity trap reactor can be used for the buffer. For example, in the case of an affinity trap reactor of the present invention bound with bacillolysin MA for the enzyme and lysine for the molecule that specifically binds with its substrate, the reactor is washed with Buffer C containing roughly 1 M NaCl and roughly 200 mM 6-aminohexanoic acid, and stored in Buffer C containing about 0.02% sodium azide. As a result of washing and storing under these conditions, an affinity trap reactor of the present invention can be used repeatedly over the course of several months.

Although the above has provided a description of the methods of producing and using an affinity trap reactor of the present invention, the present invention also relates to a single-stage process for obtaining BL-angiostatin from plasminogen contained in a biological sample using this affinity trap reactor. In this process, BL-angiostatin is obtained by applying a biological sample containing plasminogen to an affinity trap reactor composed of a support bound with bacillolysin MA and lysine, and reacting at a temperature of about 0 to 50° C., and preferably about 4 to 25° C., under conditions in the presence of isopropyl alcohol but in the absence of calcium ions. Although lysine specifically binds with both the substrate, plasminogen and the desired degradation product, BL-angiostatin, it does not bind with the by-product, mini-plasminogen. Consequently, since this by-product is removed from the affinity trap reactor without being specifically bound to the support through the lysine following the enzyme reaction, only the target product can be selectively recovered. By allowing the enzyme reaction to proceed using an affinity trap reactor of the present invention under these specific conditions, BL-angiostatin can be obtained from plasminogen at high purity and in a single stage.

The process of the present invention can be carried out according to the aforementioned method for using an affinity trap reactor of the present invention, by using an affinity trap reactor of the present invention previously described in detail. Since the concrete and detailed conditions for obtaining BL-angiostatin from plasminogen in a single stage are as described in the following examples, the present invention can be carried out based on the descriptions of the examples.

EXAMPLES

The following provides a detailed explanation of the present invention, but the present invention is not limited to the descriptions of the examples.

Example 1

Production and Purification of Bacillolysin MA

Bacillolysin MA was isolated and purified from *Bacillus megaterium* A9542 strain according to the following method. *Bacillus megaterium* A9542 was deposited on March 21, 2001 in the Ministry of Economic Trade and Industry Agency of Industrial Science and Technology, National Institute of Bioscience and Human Technology (presently the International Patent Organism Depositary (IPOD), National Institute of Advanced Industrial Science and Technology (AIST), Tsukuba Central 6,1-1-1 Higashi, Tsukuba, Ibaraki, 305-8566,Japan) and was assigned the deposit No. FERM P-18268.

After shake culturing *Bacillus megaterium* strain A9542 for 6 days at 28° C. in a 500 ml Erlenmeyer flask containing 100 ml of a liquid medium (pH 7.0) containing 1% glucose, 3% cornstarch, 1% soybean meal, 0.5% peptone, 0.5% yeast extract, 0.2% $CaCO_3$ and 0.01% CB442, 3 liters of culture liquid were filtered using celite and 1 liter of the filtrate was diluted with $H_2O$ to 5 liters followed by the addition of isopropyl alcohol to a final concentration of 5% (v/v). Subsequently, the diluted filtrate was injected at a flow rate of 15 ml/min into 400 ml of a carboxymethyl cellulose (CM-Cellulose, Seikagaku Corp.) column equilibrated with 20 mM MES (2-[N-morpholino]ethanesulfonic acid)-NaOH buffer (pH 6.5) and 5% isopropyl alcohol. After washing with 600 ml of the same buffer, the column was eluted with 20 mM MES/NaOH (pH 6.5), 5% isopropyl alcohol and 0.2 M NaCl. The eluted fractions were fractionated in 60 ml aliquots, and those fractions that demonstrated activity were combined. The purity was confirmed by SDS-PAGE, and 90 mg of purified product was obtained.

Example 2

Production of Affinity Trap Reactor of the Present Invention Immobilized with Bacillolysin MA and Lysine (Production of 10 ml of Reactor)

2.86 g of agarose gel (Sepharose 4B, Pharmacia) pre-activated with cyanogen bromide was suspended in 100 ml of 1 mM aqueous HCl solution, and stirred for 15 minutes at room temperature. This was then transferred to a column, the HCl solution was removed by aspiration, and the column was washed three times with 100 ml of 1 mM HCl solution and then once with 75 ml of Buffer A (0.1 M sodium hydrogen bicarbonate, pH 8.3) containing 0.5 M NaCl and 5% isopropyl alcohol. 2.84 mg/ml bacillolysin MA solution was prepared with the same Buffer A, and 17.6 ml of the solution was added to the column to carry out an immobilization reaction by stirring for 2 hours at room temperature. Following completion of the reaction, the solution was removed by aspiration and 20 ml of 5% aqueous isopropyl alcohol solution containing 0.2 M L-lysine hydrochloride (pH 8.0) was added to carry out a lysine immobilization reaction by stirring for 2 hours at room temperature. Following completion of this reaction, the solution was removed by aspiration, the column was washed with 500 ml of Buffer B containing 5% isopropyl alcohol (20 mM MES (2-[N-morpholino]ethanesulfonic acid)-NaOH), and then finally stored at 4° C. in Buffer B having the aforementioned composition containing 0.02% sodium azide.

Example 3

Single-Stage Purification Process of BL-Angiostatin from Human Plasma Using Bacillolysin MA/Lysine Reactor 5 ml of isopropyl alcohol was added over ice to 95 ml of citrated human plasma, and after allowing to stand for 30 minutes, supernatant was obtained by centrifugation (22,000×g, 4° C., 1 hour) and then filtered. All of the following procedures were carried out at 4° C. 10 ml of a bacillolysin MA/lysine reactor of the present invention produced in Example 2 was equilibrated with Buffer C containing 5% isopropyl alcohol (50 mM sodium phosphate, pH 7.4). The aforementioned supernatant was added to the equilibrated reactor at a flow rate of 1.5 ml/min. Subsequently, the reactor was washed (at 3 ml/min) with 200 ml of Buffer C of the aforementioned composition containing 0.5 M NaCl. Elution of the formed BL-angiostatin was carried out with 50 ml of 5% aqueous isopropyl alcohol solution containing 200 mM 6-aminohexanoic acid. As a result, nearly all of the BL-angiostatin was eluted with 10 to 30 ml of eluate. The yield of BL-angiostatin was 4.2 mg, and its purity was 95%.

Furthermore, following its use, the reactor was washed at 4° C. using 50 ml of Buffer C having the aforementioned composition containing 1 M NaCl and 200 mM 6-aminohexanoic acid. Subsequently, it was stored at 4° C. in Buffer C containing 0.02% sodium azide. As a result of being washed and stored in this state, the reactor was able to be used repeatedly for two months or longer.

3 µg of the resulting BL-angiostatin was dissolved in purified water to a volume of 10 µl, this solution was then added to 10 µl of sample buffer (125 mM Tris-HCl buffer containing 4% SDS, 10% 2-mercaptoethanol, 20% sucrose and 0.004% bromophenol blue, pH 6.8), and after fractionating 15 μl of this mixture by electrophoresis using 7.5% polyacrylamide gel, the product was stained with Coumassie Brilliant Blue R250. Those results are shown in Lane 2 of FIG. 1.

As shown in the drawing, BL-angiostatin obtained from human plasma plasminogen using an affinity trap reactor of the present invention was nearly completely free of plasminogen, by-products and other plasma proteins, and obtained at high purity.

Comparative Example 1

Degradation Reaction of Plasminogen by Bacillolysin MA

Bacillolysin MA (5 nM) and 50 mM Tris-HCl buffer (pH 7.4) containing plasminogen (3 μM), 100 mM NaCl, 0.01% Tween 80 and 1 mM $CaCl_2$ were incubated for 60 minutes at 37° C. Subsequently, 10 μl of this mixture was added to 10 μl of sample buffer (125 mM Tris-HCl buffer (pH 6.8) containing 4% SDS, 10% 2-mercaptoethanol, 20% sucrose and 0.004% bromophenol blue), and after fractionating 15 μl of this mixture by electrophoresis using 7.5% polyacrylamide gel, the product was stained with Coumassie Brilliant Blue R250. Those results are shown in Lane 1 of FIG. 1.

As shown in the drawing, in a method in which plasminogen is degraded directly by bacillolysin, unreacted plasminogen and a by-product, mini-plasminogen were contained in the degradation product in addition to BL-angiostatin, thereby preventing angiostatin from being obtained at high purity.

INDUSTRIAL APPLICABILITY

When an affinity trap reactor of the present invention is used, the reaction between enzyme and substrate bound to a support proceeds efficiently without its applications being restricted by the type of enzyme and substrate used. Moreover, by using a reactor bound with bacillolysin MA and lysine for this reactor, the reaction between bacillolysin MA and substrate plasminogen and the process through purification of the resulting product BL-angiostatin can be carried out in a single stage.

The invention claimed is:

1. An affinity trap reactor comprising:
   (a) an enzyme, wherein said enzyme is the protease bacillolysin MA obtained from *Bacillus megaterium*;
   (b) a molecule that specifically binds with a substrate of said enzyme, said molecule selected from the group consisting of lysine and hirudine; and
   (c) a support,
wherein each of said enzyme (a) and said molecule (b) are immobilized to said support (c).

2. The affinity trap reactor of claim 1, wherein the substrate is plasminogen and the molecule that specifically binds with said substrate is lysine.

3. The affinity trap reactor of claim 1, wherein the substrate is prothrombin and the molecule that specifically binds with said substrate is hirudine.

4. The affinity trap reactor of claim 1, wherein the support (c) is selected from the group consisting of a porous silica bead, cellulose, agarose, cross-linked dextran, and cross-linked polyacrylamide.

5. The affinity trap reactor of claim 4, wherein the support (c) is agarose and wherein said agarose is an agarose gel.

6. The affinity trap reactor of claim 5, wherein the molecule (b) is lysine.

7. The affinity trap reactor of any one of claims 1-6, wherein the *Bacillus megaterium* is *Bacillus megaterium* strain A9542.

8. The affinity trap reactor of claim 6, wherein the affinity trap reactor is produced by the method comprising:
   (i) contacting an agarose gel with an HCl solution, wherein said gel is an activated agarose gel activated by contacting with a cyanogen halide;
   (ii) providing a bicarbonate buffer containing isopropyl alcohol;
   (iii) washing said agarose gel of step (i) with said bicarbonate buffer of step (ii) thereby providing a washed gel; and,
   (iv) contacting said washed gel with a solution comprising bacillolysin MA enzyme and with a solution comprising L-lysine hydrochloride, wherein contacting said washed gel with said enzyme and with said lysine provides an affinity trap reactor, said reactor comprising each of said enzyme and said lysine immobilized to said washed gel.

9. A single-stage process of obtaining BL-angiostatin from a plasminogen-containing biological sample, the method comprising:
   (i) providing the affinity trap reactor of claim 2;
   (ii) applying a biological sample containing plasminogen to said trap reactor;
   (iii) contacting the bacillolysin MA enzyme of said trap reactor with said plasminogen at a temperature of 0 to 50° C., in the presence of isopropyl alcohol, and in the absence of calcium ions, thereby providing BL-angiostatin; and
   (iv) eluting said BL-angiostatin formed by the reaction of the bacillolysin MA and the plasminogen of step (iii) thereby obtaining BL-angiostatin.

10. A single-stage process of obtaining BL-angiostatin from a plasminogen-containing biological sample, the method comprising:
   (i) providing the affinity trap reactor of claim 5;
   (ii) applying a biological sample containing plasminogen to said trap reactor;
   (iii) contacting the bacillolysin MA enzyme of said trap reactor with said plasminogen at a temperature of 0 to 50° C., in the presence of isopropyl alcohol, and in the absence of calcium ions, thereby providing BL-angiostatin; and
   (iv) eluting said BL-angiostatin formed by the reaction of the bacillolysin MA and the plasminogen of step (iii), thereby obtaining BL-angiostatin.

11. The process according to any one of claims 9 or 10, wherein in step (iii) the temperature is 4 to 25° C.

* * * * *